United States Patent
Ohyu et al.

(10) Patent No.: US 8,374,410 B2
(45) Date of Patent: Feb. 12, 2013

(54) MEDICAL IMAGE DISPLAY DEVICE AND IMAGE DISPLAYING METHOD

(75) Inventors: Shigeharu Ohyu, Yaita (JP); Hitoshi Yamagata, Otawara (JP); Arturo Calderon, Otawara (JP); Atsuko Sugiyama, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 704 days.

(21) Appl. No.: 12/525,315

(22) PCT Filed: Feb. 12, 2009

(86) PCT No.: PCT/JP2009/052318
§ 371 (c)(1),
(2), (4) Date: Jul. 31, 2009

(87) PCT Pub. No.: WO2009/104510
PCT Pub. Date: Aug. 27, 2009

(65) Prior Publication Data
US 2011/0158487 A1 Jun. 30, 2011

(30) Foreign Application Priority Data
Feb. 19, 2008 (JP) .................... 2008-037673

(51) Int. Cl.
*G06K 9/00* (2006.01)
(52) U.S. Cl. ......................................... 382/128
(58) Field of Classification Search ............ 382/128
See application file for complete search history.

(56) References Cited

U.S. PATENT DOCUMENTS

2007/0217665 A1* 9/2007 Kiraly et al. ............ 382/128
2008/0019580 A1    1/2008 Ohyu et al.

FOREIGN PATENT DOCUMENTS

| JP | 8-131403 | 5/1996 |
|---|---|---|
| JP | 2005-334219 | 12/2005 |
| JP | 2007-54636 | 3/2007 |
| WO | WO2005/010793 A1 * | 2/2005 |

OTHER PUBLICATIONS

Jeongtae Kim, et al., "Intensity-Based Image Registration Using Robust Correlation Coefficients", IEEE Transactions on Medical Imaging, vol. 23, No. 11, Nov. 2004, pp. 1430-1444.
Hidenori Shikata, et al., "Algorithm for Localizing Points of Pulmonary Vessels for Non-rigid Registration in Lung", IEICE Transactions, vol. J85-D-II, No. 10, 2002, 6 pages (with English Abstract).

* cited by examiner

*Primary Examiner* — John Pauls
(74) *Attorney, Agent, or Firm* — Oblon, Spivak, McClelland, Maier & Neustadt, L.L.P.

(57) ABSTRACT

A reference landmark extracting and pairing unit extracts reference landmarks from each of two three-dimensional medical images and forms reference landmark pairs, while a general landmark extracting unit extracts general landmarks. The landmark pair forming unit forms general landmark pairs using of a distance between each of the reference landmarks and the general landmarks, and also forms general landmark pairs from the remaining general landmarks using the distances from the general landmarks included in the general landmark pairs. A coordinate transformation parameter calculating unit calculates coordinate transformation parameters, based on the positional information of the reference landmark pairs and the general landmark pairs. A corresponding sectional view creating unit creates corresponding sectional views for the two three-dimensional medical images based on the coordinate transformation parameters, and by the display controlling unit the two corresponding sectional views are displayed on a displaying unit.

11 Claims, 13 Drawing Sheets

FIG.2
(A)
THRESHOLD PROCESSING
EXTRACT REGIONS
HAVING PIXEL VALUES EQUAL
TO OR SMALLER THAN -950 H.U.
GAP-FILLING PROCESSING
AND CONNECTED AREA
EXTRACTING PROCESSING
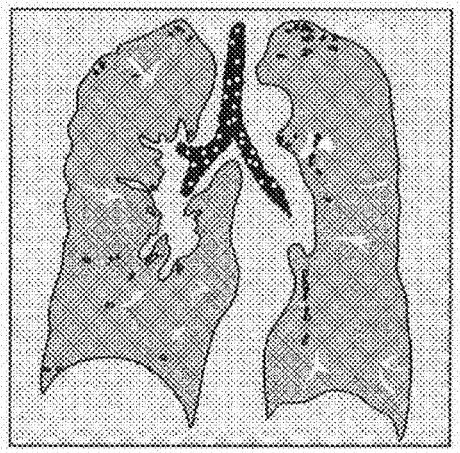 → 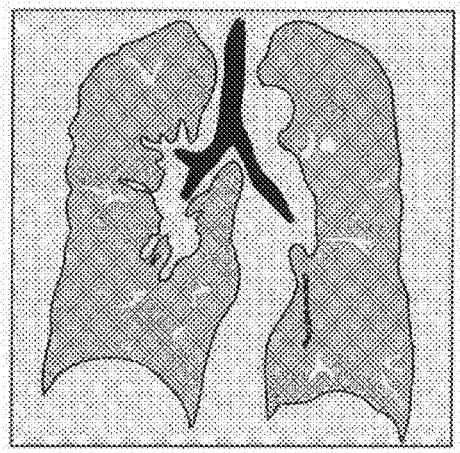
(B)
BRANCHING POINT
DETECTION PROCESSING
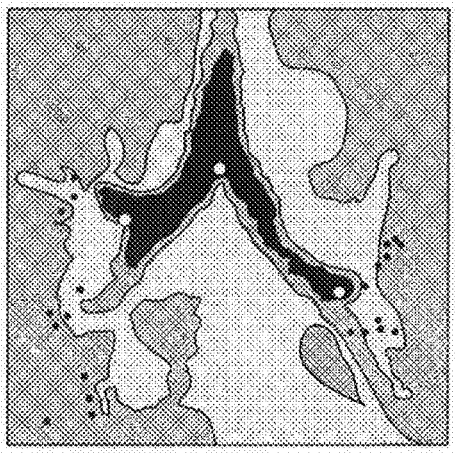

FIG.3
(A)
PAST THREE-DIMENSIONAL MEDICAL IMAGE (IMAGE A)
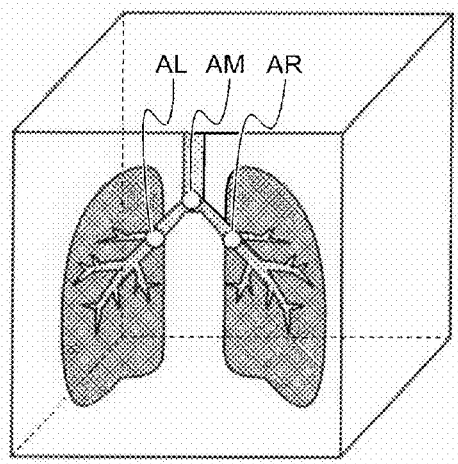
RECENT THREE-DIMENSIONAL MEDICAL IMAGE (IMAGE B)
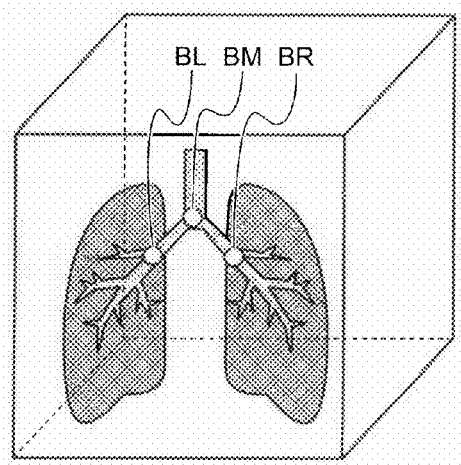
(B)
|  | REFERENCE LANDMARK OF IMAGE A | REFERENCE LANDMARK OF IMAGE B |
| --- | --- | --- |
| REFERENCE LANDMARK PAIR 1 | AM | BM |
| REFERENCE LANDMARK PAIR 2 | AL | BL |
| REFERENCE LANDMARK PAIR 3 | AR | BR |

FIG.6

LANDMARK PAIR 1
$t11-r11=a1r11+b1r12+c1r13+d1$
$t12-r12=a2r11+b2r12+c2r13+d2$
$t13-r13=a3r11+b3r12+c3r13+d3$

LANDMARK PAIR 2
$t21-r21=a1r21+b1r22+c1r23+d1$
$t22-r22=a2r21+b2r22+c2r23+d2$
$t23-r23=a3r21+b3r22+c3r23+d3$

⋮

LANDMARK PAIR m
$tm1-rm1=a1rm1+b1rm2+c1rm3+d1$
$tm2-rm2=a2rm1+b2rm2+c2rm3+d2$
$tm3-rm3=a3rm1+b3rm2+c3rm3+d3$

EXTRACT BRONCHI BRANCHING POINTS
OTHER THAN MAJOR 3 BRANCHING POINTS
AS GENERAL LANDMARKS

FIG.12

LANDMARK PAIR 1
$w_1(t_{11}-r_{11})=w_1(a_1r_{11}+b_1r_{12}+c_1r_{13}+d_1)$
$w_1(t_{12}-r_{12})=w_1(a_2r_{11}+b_2r_{12}+c_2r_{13}+d_2)$
$w_1(t_{13}-r_{13})=w_1(a_3r_{11}+b_3r_{12}+c_3r_{13}+d_3)$

LANDMARK PAIR 2
$w_2(t_{21}-r_{21})=w_2(a_1r_{21}+b_1r_{22}+c_1r_{23}+d_1)$
$w_2(t_{22}-r_{22})=w_2(a_2r_{21}+b_2r_{22}+c_2r_{23}+d_2)$
$w_2(t_{23}-r_{23})=w_2(a_3r_{21}+b_3r_{22}+c_3r_{23}+d_3)$

⋮

LANDMARK PAIR m
$w_m(t_{m1}-r_{m1})=w_m(a_1r_{m1}+b_1r_{m2}+c_1r_{m3}+d_1)$
$w_m(t_{m2}-r_{m2})=w_m(a_2r_{m1}+b_2r_{m2}+c_2r_{m3}+d_2)$
$w_m(t_{m3}-r_{m3})=w_m(a_3r_{m1}+b_3r_{m2}+c_3r_{m3}+d_3)$

MEDICAL IMAGE DISPLAY DEVICE AND IMAGE DISPLAYING METHOD

TECHNICAL FIELD

The present invention relates to a medical image display device and an image displaying method.

BACKGROUND ART

In conventional technologies, progression and severity of a disease are understood by comparing and interpreting medical images of the same patient that are obtained at different periodically times so that treatment strategy can be determined.

For example, when a medical image photographed in a recent examination (recent image) is compared with another medical image photographed in a previous examination (past image) for interpretation, the recent image and the past image are displayed at a time by use of an image display software program having a function of loading multiple images in and displaying the images on a screen.

In addition, Patent Document 1 discloses an image diagnosis assisting apparatus that extracts a marker such as an abnormal shadow from a medical image and superimposes the extracted marker on the medical image, thereby facilitating understanding of the progression or severity of a disease from comparison and interpretation of a recent image and a past image.

In the comparison and interpretation, it is important to compare sectional images of substantially the same position of a patient, and registration should be performed on medical images of different photographing times. Furthermore, recent medical image diagnosis apparatus including X-ray CT apparatus is capable of creating three-dimensional medial images from sectional images obtained by photographing a patient, and thus registration is required for the three-dimensional medical images.

As methods commonly used for the registration between images, repetitive registration adopting image similarities and registration adopting landmarks are well known.

With the repetitive registering method adopting image similarities, the registration between the images is repeatedly performed by using image similarities such as similarity coefficients (see Non-Patent Document 1, for example). More specifically, dozens of local areas are determined in each of the three-dimensional medical images that are to be compared, and then correspondence between the local areas of the three-dimensional medical images is determined so that image similarities can be calculated for each pair of local areas. Furthermore, processes such as parallel shift, rotation, scaling (resizing), and shape altering are repeatedly performed on the images in such a manner to increase the image similarity. The registration of the three-dimensional medical images is thereby achieved. This repetition of the processes, however, requires a long time, and thus the registration between the three-dimensional medical images cannot be performed at high speed in accordance with the repetitive registering method incorporating image similarities.

On the other hand, with the landmark registering method, a pair of landmarks for the recent and past images are selected from extracted landmarks of the recent image and of the past image to perform the registration. In comparison with the repetitive registration adopting image similarities, the processing time can be shortened by adopting linear optimization for the registration of landmarks. For example, Non-Patent Document 2 discloses a technology of extracting branching points of the lung blood vessels or trachea as landmarks from chest CT images. By using the extracted branching points of the lung blood vessels or trachea as landmarks in accordance with this technology, the registration of the recent and past chest CT images can be established at high speed.

Patent Document 1:Japanese Patent Application Laid-open No. 2005-334219

Non-Patent Document 1:Jeongtae Kim, Jefferey A. Fessl, "Intensity-based image registration using robust correlation coefficients", IEEE Transactions on Medical Imaging, Vol. 23, November 2004, pp. 1430-1444

Non-Patent Document 2:Hidenori Shikata, et al. "Algorithm for Localizing Points of Pulmonary Vessels for Non-rigid Registration in Lung", IEICE Transactions, Vol. J85-D-II, No. 10, pp. 1613-1623, 2002

DISCLOSURE OF INVENTION

Problem to be Solved by the Invention

With the aforementioned landmark registering method, the registration between three-dimensional medical images cannot be always accurately achieved.

For example, if a patient has been in bed for along period of time due to hospitalization or the like, body water and blood tends to be shifted toward the bed. When a chest CT image of the patient in such conditions is taken, a high absorption area may appear in the lung area, as illustrated in FIG. 13, because the accumulated water and blood absorbs X-ray, which turns the lung area white. In case of complicating pneumonia, a high absorption area may also appear in the lung area. FIG. 13 is a diagram for explaining the problem in the conventional technology.

When branching points of the lung blood vessels are extracted from a chest CT image that turns out to be an error image with a high absorption area in the lung area, a number of "points that are not branching points of the lung blood vessels", or in other words a number of "false branching points", are erroneously extracted along with the branching points of the lung blood vessels, as shown in FIG. 13. If the extracted false branching points are used as landmarks, pairs of landmarks cannot be accurately chosen from the recent and past images, and as a result, the registration cannot be accurately performed between the three-dimensional medical images.

More specifically, with the aforementioned landmark registering method, when an abnormal image as indicated in FIG. 13 is to be processed, a problem resides in that the registration cannot be accurately performed between the three-dimensional medical images because of many errors included in the extracted landmarks.

Hence, the present invention has been conceived to solve the above problem in the conventional technology. The purpose of the present invention is to offer a medical image display device and an image displaying method for always accurately achieving registration between three-dimensional medical images.

Means for Solving Problem

According to one aspect of the present invention, a medical image display device, comprising: a reference feature point extracting and pairing unit that extracts reference feature points that are feature points indentifying association and serving as references in registration individually from a first and a second three-dimensional medical images, and forms a reference feature point pair in which extracted reference feature points are associated with each other; a general feature point extracting unit that extracts general feature points that are feature points possible to use in the registration individually from the first and the second three-dimensional medical images; a general feature point pairing unit that forms a general feature point pair in which association is established between the first and the second three-dimensional medical images, from the general feature points extracted by the general feature point extracting unit, based on positional relationship with respect to the reference feature points extracted by the reference feature point extracting and pairing unit individually from the first and the second three-dimensional medical images; a coordinate transformation parameter determining unit that determines a coordinate transformation parameter that is to be used to perform the registration between the first and the second three-dimensional medical images, based on positional information of the reference feature point pair for which the association is established by the reference feature point extracting and pairing unit and the general feature point pair for which the association is established by the general feature point pairing unit; a corresponding image creating unit that creates corresponding images for the first and the second three-dimensional medical images, based on the coordinate transformation parameter determined by the coordinate transformation parameter determining unit; and a display controlling unit that perform control so that the corresponding images of the first and the second three-dimensional medical images created by the corresponding image creating unit are displayed on a predetermined displaying unit.

According to another aspect of the present invention, an image displaying method, comprising: a reference feature point extracting and pairing step of extracting reference feature points that are feature points indentifying association and serving as references in registration individually from a first and a second three-dimensional medical images, and forming a reference feature point pair in which extracted reference feature points are associated with each other; a general feature point extracting step of extracting general feature points that are feature points possible to use in the registration individually from the first and the second three-dimensional medical images; a general feature point pairing step of forming a general feature point pair in which association is established between the first and the second three-dimensional medical images from the general feature points extracted at the general feature point extracting step, based on positional relationship with respect to the reference feature points extracted from each of the first and the second three-dimensional medical images at the reference feature point extracting and pairing step; a coordinate transformation parameter determining step of determining a coordinate transformation parameter that is to be used to perform the registration between the first and the second three-dimensional medical images, based on positional information of the reference feature point pair for which the association is established at the reference feature point extracting and pairing step and the general feature point pair for which the association is established at the general feature point pairing step; a corresponding image creating step of creating corresponding images for the first and the second three-dimensional medical images, based on the coordinate transformation parameter determined at the coordinate transformation parameter determining step; and a display controlling step of performing control so that the corresponding images of the first and the second three-dimensional medical images created at the corresponding image creating step are displayed on a predetermined displaying unit.

Effect of the Invention

According to the present invention, the registration between three-dimensional medical images can be always accurately performed.

BRIEF DESCRIPTION OF DRAWINGS

FIG. 2 is a diagram for explaining a reference landmark extracting and pairing unit.

FIG. 3 is a diagram for explaining the reference landmark extracting and pairing unit.

FIG. 6 is a diagram for explaining a coordinate transformation parameter calculating unit according to the first embodiment.

FIG. 12 is a diagram for explaining a coordinate transformation parameter calculating unit according to a third embodiment.

Figure 1:
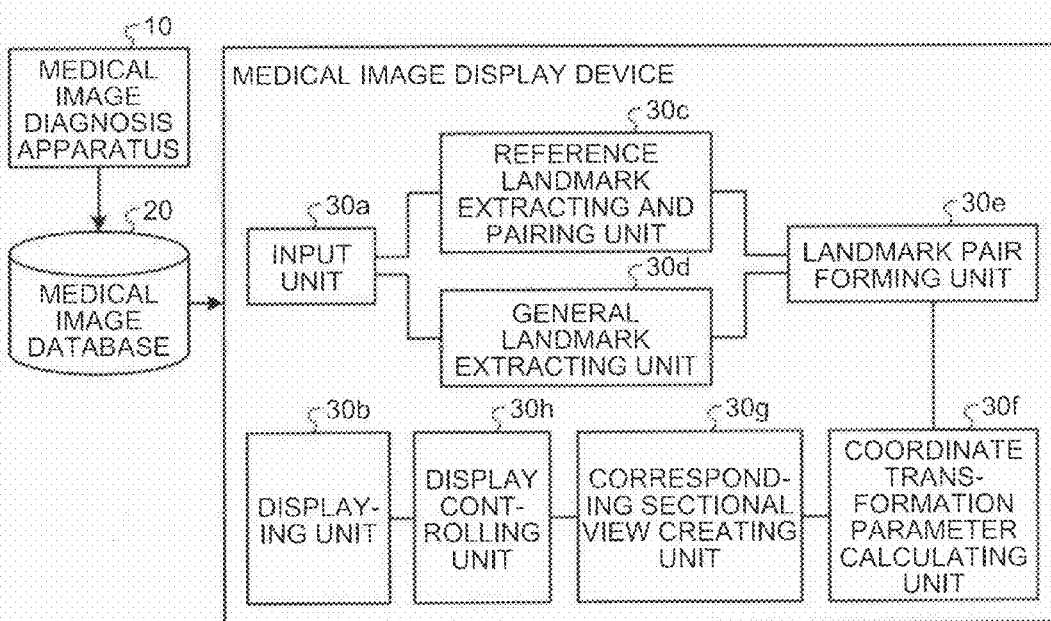
FIG. 1 is a diagram for explaining a structure of a medical image display device according to a first embodiment.

EXPLANATIONS OF LETTERS OR NUMERALS 10 medical image diagnosis apparatus
20 medical image database
30 medical image display device
30a input unit
30b displaying unit
30c reference landmark extracting and pairing unit
30d general landmark extracting unit
30e landmark pair forming unit
30f coordinate transformation parameter calculating unit
30g corresponding sectional view creating unit
30h display controlling unit

BEST MODE(S) FOR CARRYING OUT THE INVENTION

Exemplary embodiments of a medical image display device and an image displaying method according to the present invention are explained in detail below with reference to the attached drawings.

[First Embodiment]

First, the structure of the medical image display device according to the first embodiment is explained. FIG. 1 is a diagram for showing the structure of the medical image display device according to the first embodiment. As illustrated in FIG. 1, a medical image display device 30 according to the first embodiment includes an input unit 30a, a displaying unit 30b, a reference landmark extracting and pairing unit 30c, a general landmark extracting unit 30d, a landmark pair forming unit 30e, a coordinate transformation parameter calculating unit 30f, a corresponding sectional view creating unit 30g, and a display controlling unit 30h.

In outline, the medical image display device 30 according to the first embodiment reads two three-dimensional medical images designated by way of the input unit 30a by a user such as a doctor who conducts comparison and interpretation, from multiple three-dimensional medical images created by a medical image diagnosis apparatus 10 and stored in a medical image database 20, as illustrated in FIG. 1. Then, it performs registration on the two three-dimensional medical images and displays corresponding sectional view images (hereinafter, "corresponding sectional views") on the displaying unit 30b. The characteristic feature resides in that registration of the three-dimensional medical images can be always accurately achieved.

Figure 4:
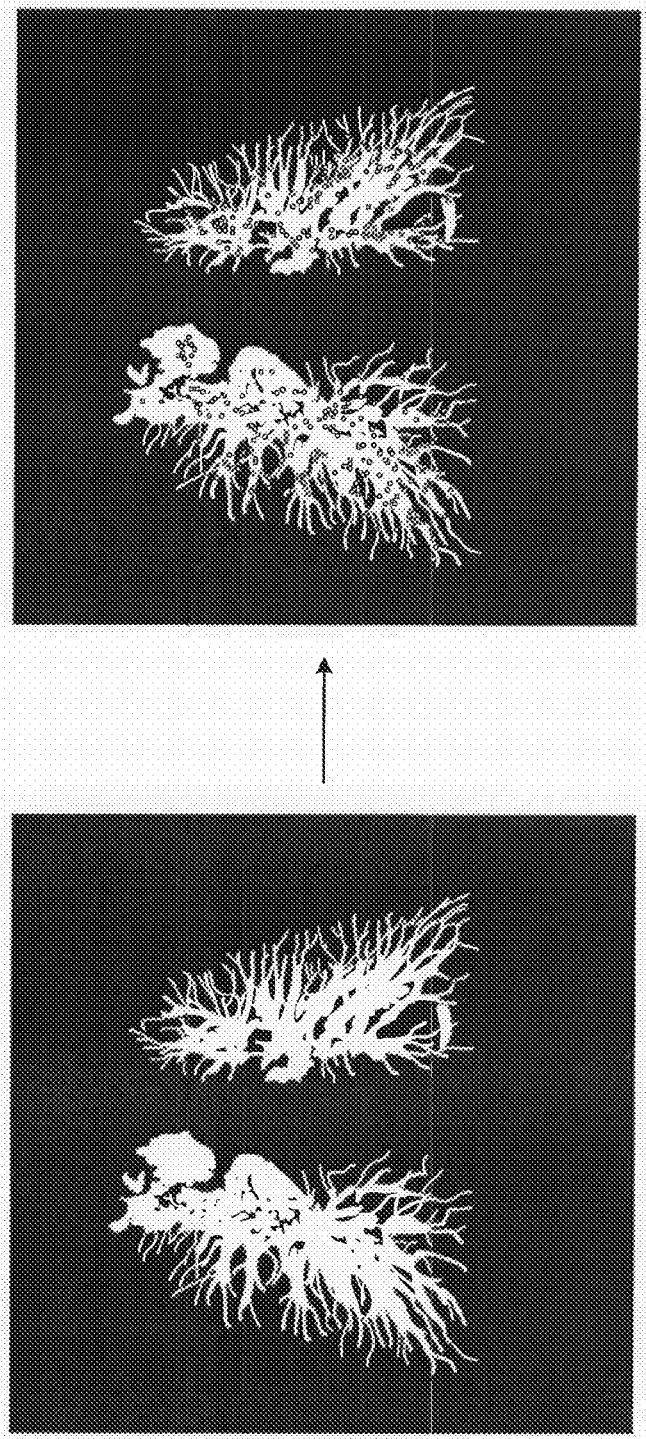
FIG. 4 is a diagram for explaining a general landmark extracting unit according to the first embodiment.
Figure 5:
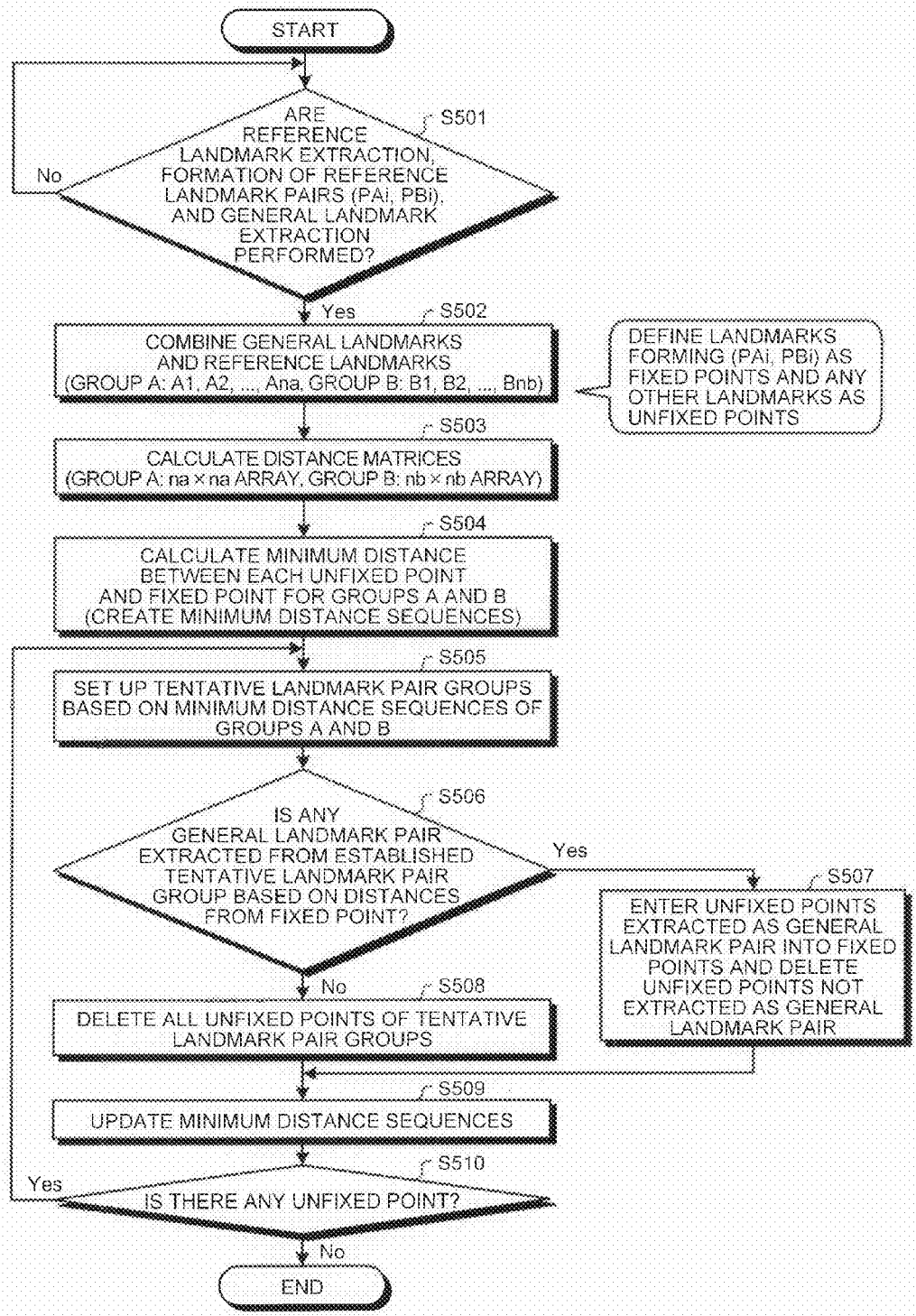
FIG. 5 is a diagram for explaining a process performed at a landmark pair forming unit.
Figure 7:
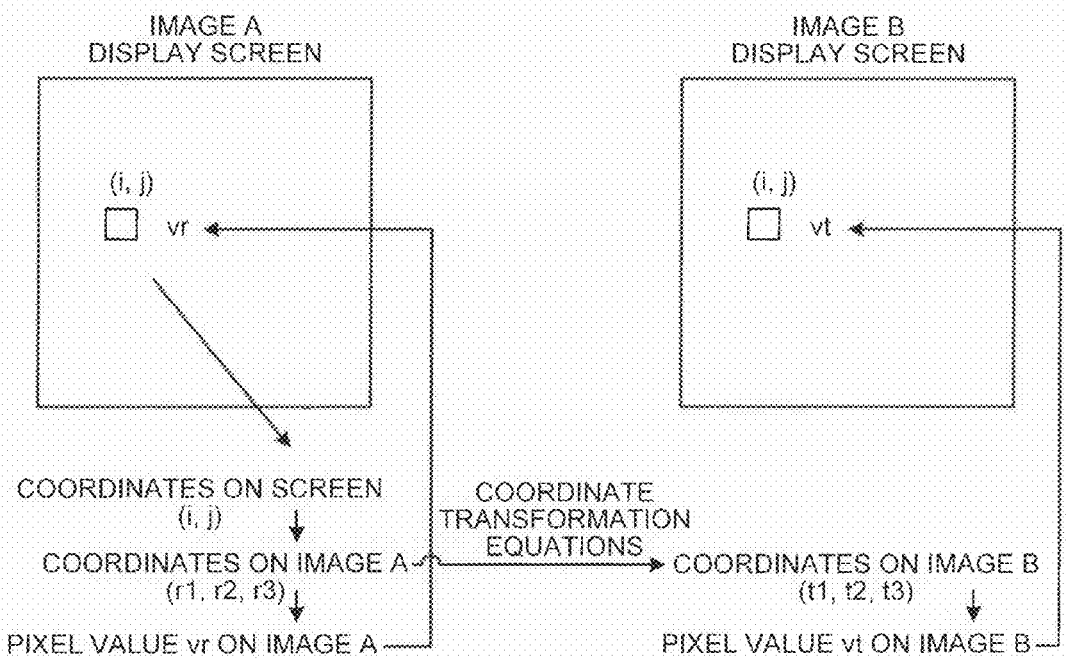
FIG. 7 is a diagram for explaining a corresponding sectional view creating unit.

The above main feature is explained with reference to FIGS. 2 to 7, as well as to FIG. 1. FIGS. 2 and 3 are diagrams for explaining the reference landmark extracting and pairing unit, and FIG. 4 is a diagram for explaining the general landmark extracting unit according to the first embodiment. FIG. 5 is a diagram for explaining the process performed at the landmark pair forming unit, and FIG. 6 is a diagram for explaining the coordinate transformation parameter calculating unit according to the first embodiment. FIG. 7 is a diagram for explaining the corresponding sectional view creating unit.

Examples of the medical image diagnosis apparatus 10 include an MRI apparatus, an X-ray CT apparatus, a nuclear medical diagnosis apparatus, and an ultrasound diagnosis apparatus. Examples of the medical image database 20 include a database of the Picture Archiving and Communication System (PACS), which is a system for managing various types of medical image data, and a database of an electronic chart system for managing electronic charts to which medical images are attached.

The explanation of the present embodiment focuses on an example in which the medical image display device 30 performs registration on three-dimensional medical images including the lung that are created by an X-ray CT apparatus that serves as the medical image diagnosis apparatus 10 in past and recent chest CT examinations of the same patient, and displays corresponding sectional views on the displaying unit 30b. Moreover, in the following explanation, a three-dimensional medical image generated in the past examination by the X-ray CT apparatus that serves as the medical image diagnosis apparatus 10 is referred to as a past three-dimensional medical image, while a three-dimensional medical image generated in the recent examination by the X-ray CT apparatus that serves as the medical image diagnosis apparatus 10 is referred to as a recent three-dimensional medical image. It should be noted that the past three-dimensional medical image corresponds to the "first three-dimensional medical image" recited in the claims, and that the recent three-dimensional medical image corresponds to the "second three-dimensional medical image" recited in the claims.

The reference landmark extracting and pairing unit 30c extracts, from each of the past three-dimensional medical image and the recent three-dimensional medical image, a reference landmark that is a landmark used as a registration reference and for which the correspondence is uniquely determined from an anatomical aspect, and pairs the extracted reference landmarks that correspond to each other (reference landmark pair). Here, the landmark corresponds to the "feature point" recited in the claims, and similarly, the reference landmark corresponds to the "reference feature point". Similarly, the reference landmark pair corresponds to the "reference feature point pair", and the reference landmark extracting and pairing unit 30c corresponds to the "reference feature point extracting and pairing unit".

More specifically, the reference landmark extracting and pairing unit 30c extracts, as reference landmarks, three major branching points of the trachea and bronchi. In particular, the reference landmark extracting and pairing unit 30c extracts, as the three major branching points, the branching point of the trachea and the first branching points of the left and right bronchi. First, the reference landmark extracting and pairing unit 30c performs threshold processing to extract main portions of the trachea and bronchi from each of the past three-dimensional medical image and the recent three-dimensional medical image. In other words, by referring to a threshold value of, for example, "−950 Hounsfield units (H.U.)", the reference landmark extracting and pairing unit 30c extracts regions having pixel values equal to or smaller than the threshold value as the main portions of the trachea and the bronchi from the past three-dimensional medical image and the recent three-dimensional medical image, as illustrated on the left side of FIG. 2(A). Here, as illustrated on the left side of FIG. 2(A), the extracted main portions of the trachea and bronchi include a number of pixels whose pixel values are greater than the threshold value. Furthermore, pixels whose pixel values are equal to or smaller than the threshold value are scattered over areas outside the extracted main portions of the trachea and bronchi.

If the three major branching points are extracted under a condition in which a number of pixels larger than the threshold value are present in the extracted main portions of the trachea and bronchi and a number of pixels equal to or smaller than the threshold value are present in areas outside the extracted main portions of the trachea and bronchi as discussed above, false branching points can be included in the extraction.

For this reason, the reference landmark extracting and pairing unit 30c performs gap-filling processing, as illustrated on the right side of FIG. 2(A), on the pixels greater than the threshold value in the extracted main portions of the trachea and bronchi, and further performs processing for extracting a single area of the connected main portions of the trachea and bronchi by the gap-filling processing so that the pixels equal to or smaller than the threshold values that are not in the main portions of the trachea and bronchi can be eliminated.

Then, the reference landmark extracting and pairing unit 30c executes the process of extracting three major branching points on the main portion of the trachea and bronchi extracted as the connected area (hereinafter, "main area"). More specifically, the reference landmark extracting and pairing unit 30c determines a seed point that serves as a starting point for extracting the branching points of the trachea and bronchi, at the center of the main area in a sectional view image that is positioned, for example, "50 millimeters" below the top of the target three-dimensional medical image, and expands voxels of the main area layer by layer starting from the determined seed point. By this layer-by-layer expansion, the sectional view bifurcates when it reaches the branching point of the trachea or bronchi. Thus, when the sectional view branches, the preceding sectional view is determined as a branching sectional view, and the center position of the voxels of this branching sectional view is obtained and determined as a branching point.

It should be noted that branching points are extracted from the upper and lower sides with respect to the seed point. However, the branching point on the upper side is erroneously extracted by the influence of the image boundary or the like, and thus it is not an actual branching point. In other words, the reference landmark extracting and pairing unit 30c extracts the branching point that first appears on the lower side of the seed point as a "main trachea branching point" where the trachea branches off to the left and right bronchi, and then extracts, of the first two branching points (the first bronchi branching points) that are extracted next, the right one as the "first right-side branching point" and the left one as the "first left-side branching point". For example, as indicated in FIG. 2(B), the reference landmark extracting and pairing unit 30c extracts the three points indicated by white dots as the "three major branching points" of the "main trachea branching point", the "first right-side branching point", and the "first left-side branching point". In FIG. 2(B), branching points extracted besides the "three major branching points" are indicated by black dots. According to the above processing, the "three major branching points" can be always accurately extracted and used as the reference in registration.

In this manner, after extracting the three reference landmarks including the "three major branching points" from each of the past three-dimensional medical image and the recent three-dimensional medical image, the reference landmark extracting and pairing unit 30c forms reference landmark pairs. For example, the reference landmark extracting and pairing unit 30c defines the "main trachea branching point" extracted from an "image A", which is the past three-dimensional medical image, as "AM"; the "first right-side branching point" as "AR"; and the "first left-side branching point" as "AL", as illustrated in FIG. 3(A). The reference landmark extracting and pairing unit 30c also defines the "main trachea branching point" extracted from an "image B", which is the recent three-dimensional medical image, as "BM"; the "first right-side branching point" as "BR"; and the "first left-side branching point" as "BL". Then, the reference landmark extracting and pairing unit 30c associates, as indicated in FIG. 3(B), "AM" with "BM" to form a "reference landmark pair 1"; "AL" with "BL" to form a "reference landmark pair 2"; and "AR" with "BR" to form a "reference landmark pair 3".

In FIG. 1, the general landmark extracting unit 30d extracts, from each of the past three-dimensional medical image and the recent three-dimensional medical image, branching points of the lung blood vessels as general landmarks that may be used for registration. Here, a general landmark corresponds to the "general feature point" recited in the claims, and similarly, the general landmark extracting unit 30d corresponds to the "general feature point extracting unit".

More specifically, first, the general landmark extracting unit 30d extracts an image area corresponding to the lung (lung image area) from each of the past three-dimensional medical image and the recent three-dimensional medical image, and then extracts areas equal to or higher than "−600 H.U." from the lung image area. The extracted area equal to or higher than "−600 H.U." is defined as an area of the lung blood vessels (lung blood vessel area) (see the left side of FIG. 4). Then, the general landmark extracting unit 30d determines the seed point in the boundary portion with the heart that is included in the lung blood vessel area, and performs a process of extracting lung blood vessel branching points in the same manner as the trachea branching point extracting process (see the right side of FIG. 4). Here, the extracted branching points of the lung blood vessels are indicated by circles on the right side of FIG. 4. In FIG. 4, the results of the extraction process of the lung blood vessel area and the lung blood vessel branching points are shown in two-dimensional images for the sake of drawing, but in reality, the extraction process is performed with three-dimensional images.

It should be noted here that the points extracted as the lung blood vessel branching points according to the above process may not always be correct lung blood vessel branching points, but points in the bronchial wall and the inside of the tuber may be erroneously extracted as lung blood vessel branching points. Furthermore, the lung blood vessel branching points cannot be entirely extracted, but only part of the lung blood vessel branching points are extracted. Thus, the lung blood vessel branching points extracted by the general landmark extracting unit 30d are used in the following process as landmarks that may be employed for registration. In the following description, the branching points of the lung blood vessels extracted from the "image A" as the past three-dimensional medical image are designated as "general landmark group A", and the branching points of the lung blood vessels extracted from the "image B" as the recent three-dimensional medical image are designated as "general landmark group B".

In FIG. 1, the landmark pair forming unit 30e forms general landmark pairs in which association is established between the "image A" and the "image B" from the "general landmark group A" and the "general landmark group B" extracted by the general landmark extracting unit 30d, based on the positional relationship with the reference landmarks extracted by the reference landmark extracting and pairing unit 30c. Here, a general landmark pair corresponds to the "general feature point pair" recited in the claims, and similarly, the landmark pair forming unit 30e corresponds to the "general feature point pairing unit".

More specifically, the landmark pair forming unit 30e searches, from among the "general landmark group A" and the "general landmark group B", for general landmarks for which the difference and ratio between a distance from each of the three reference landmarks extracted from the "image A" and a distance from each of the three corresponding reference landmarks extracted from the "image B" are in a predetermined range to form a general landmark pair.

Furthermore, the landmark pair forming unit 30e forms another general landmark pair from general landmarks other than the general landmarks that are determined to form the general landmark pair, or in other words from the "general landmark group A" and the "general landmark group B" except for the general landmarks determined to form the general landmark pair, by using the distance from each of the general landmarks determined to form the general landmark pair in addition to the distance from each of the three reference landmarks.

The above process is explained by use of a specific example, with reference to FIG. 5. In the following description, "AM", "AR", and "AL" in the "image A" indicated in FIG. 3(B) are now designated as "PA1", "PA2", and "PA3", and "BM", "BR", and "BL" in the "image B" indicated in FIG. 3(B) are now designated as "PB1", "PB2", and "PB3". With the reference landmarks designated in this manner, the three reference landmark pairs can be expressed as "(PAi, PBi) (where i=1, 2, 3)".

As illustrated in FIG. 5, first, after the reference landmark extracting and pairing unit 30c extracts the reference landmarks from the "image A" and the "image B" and forms the reference landmark pairs (PAi, PBi) and the general landmark extracting unit 30d extracts the general landmarks (yes at step S501), the landmark pair forming unit 30e combines the reference landmarks with the general landmarks (step S502).

For example, when the number "na-3" of general landmarks are extracted from the "image A" and the number "nb-3" of general landmarks are extracted from the "image B", a group of landmarks in the "image A" after the combining (hereinafter, "Group A") includes "A1, A2, ..., Ana", while a group of landmarks in the "image B" after the combining (hereinafter, "Group B") includes "B1, B2, ..., Bnb". The reference landmarks that are brought into correspondence between the "image A" and the "image B" are defined as fixed points, while the general landmarks that are not brought into correspondence between the "image A" and the "image B" (at this time point, all the extracted general landmarks) are defined as unfixed points.

Then, the landmark pair forming unit 30e calculates all the distances regarding the number "na" of points included in Group A and all the distances regarding the number "nb" of points included in Group B, and obtains distance matrices for Groups A and B (step S503). Here, the distance matrix for Group A is an array of "naxna", and the distance matrix for Group B is an array of "nbxnb". In the following, the landmark pair forming unit 30e refers to these distance matrices in all the distance calculating processes to speed up the processes.

Thereafter, the landmark pair forming unit 30e searches through the distance matrices of Group A and Group B for the closest fixed point for each of the unfixed points, calculates the distance (minimum distance) from the found fixed point, and forms a minimum distance sequence by sorting the minimum distances in ascending order for the unfixed points (step S504).

Then, the landmark pair forming unit 30e sets up a tentative landmark pair group based on the minimum distance sequences of Groups A and B (step S505). For example, the landmark pair forming unit 30e establishes a tentative landmark pair group from the first to fifth unfixed points in the minimum distance sequence of Group A and the first to fifth unfixed points in the minimum distance sequence of Group B.

Based on the distances from the fixed points, the landmark pair forming unit 30e determines whether a general landmark pair can be extracted from the established tentative landmark pair group (step S506). For example, the landmark pair forming unit 30e calculates distances from the fixed points "PA1, PA2, and PA3" for the five unfixed points that are determined as the tentative landmark pair group in Group A, with reference to the distance matrix of Group A. Furthermore, distances from the fixed points "PB1, PB2, and PB3" are calculated for the five unfixed points that are determined as the tentative landmark pair group in Group B, with reference to the distance matrix of Group B. For example, when the distances between an "unfixed point TA1" determined to be included in the tentative landmark pair group of Group A and "PA1, PA2, and PA3" are "TAL1, TAL2, and TAL3", respectively, and the distances between the "unfixed point TB1" determined to be included in the tentative landmark pair group of Group B and "PB1, PB2, and PB3" are "TBL1, TBL2, and TBL3", respectively, the "unfixed point TA1" and the "unfixed point TB1" are determined as general landmarks that are associated with each other between the "image A" and the "image B", if all the distance ratios (i.e., "TAL1/TBL1", "TAL2/TBL2", and "TAL3/TBL3") are within the range between "0.9 and 1.11", and all the differences between the distances (i.e., absolute values of "TAL1-TBL1", "TAL2-TBL2", and "TAL3-TBL3") are below "3 millimeters". These two points are paired into a general landmark pair.

The above process is conducted for all the combinations of the five unfixed points that are determined as the tentative landmark pair group of Group A and the five unfixed points that are determined as the tentative landmark pair group of Group B, and whether a general landmark pair can be extracted from the established tentative landmark pair groups.

Here, when a general landmark pair is extracted from the established tentative landmark pair group (yes at step S506), the landmark pair forming unit 30e enters the unfixed points extracted as the general landmark pair into the fixed points, and deletes unfixed points that are not extracted as a general landmark pair (step S507). For example, when three pairs of unfixed points are extracted as constituent elements of general landmark pairs from the established tentative landmark pair groups each having the five points, the three pairs of unfixed points (three points from Group A and three points from Group B) are entered into the fixed points, and the four unfixed points (two points from Group A and two points from Group B) that are not extracted as general landmark pairs are deleted.

On the other hand, if no general landmark pair is extracted from the established tentative landmark pair groups (no at step S506), the landmark pair forming unit 30e deletes all the unfixed points of the tentative landmark pair groups established at step S505 (ten unfixed points in total, including five points from Group A and five points from Group B according to the present embodiment) (step S508).

Then, the landmark pair forming unit 30e updates the minimum distance sequences of Groups A and B, based on the information of the general landmarks newly entered into the fixed points together with the reference landmarks and the general landmarks deleted as unfixed points at steps S507 and S508 (step S509). In other words, a minimum distance sequence obtained from a set of fixed points having the general landmarks newly entered into the fixed points and the reference landmarks and a set of unfixed points having the general landmarks after the deletion is updated and created for each of Groups A and B.

Thereafter, the landmark pair forming unit 30e determines whether any general landmark that is an unfixed point is included in Groups A and B (step S510).

Here, if a general landmark that is an unfixed point is included in Groups A and B (yes at step S510), the landmark pair forming unit 30e returns to step S505, and sets up a tentative landmark pair group based on the updated minimum distance sequences of the Groups A and B (step S505). For example, the landmark pair forming unit 30e newly determines the first to fifth unfixed points in the updated minimum distance sequence of Group A and the first to fifth unfixed points in the updated minimum distance sequence of Group B as tentative landmark pair groups.

On the other hand, if no general landmark that is an unfixed point is included in Group A or B (no at step S510), the landmark pair forming unit 30e terminates the process.

According to the present embodiment, the use of distance matrices that have the entire information of the distances that are obtained for all the points including the reference landmarks and the general landmarks is explained. The present invention is not limited thereto, however. For example, the distance matrices may be the calculated distance information from which information of distances equal to or larger than a certain length, or of distances equal to or smaller than a certain length, is deleted. In this manner, an unnecessary associating operation of general landmarks can be further avoided.

In addition, in the explanation according to the present embodiment, the distance information of the unfixed points and the fixed points only are adopted as the reference to determine whether they form a general landmark pair. However, the present invention is not limited thereto. Unnecessary general landmark pairs may be deleted by making a judgment in accordance with additional further strict references. In particular, whether a general landmark pair is formed may be further strictly judged by using information of an angle between the fixed point and each of the unfixed points that are determined as forming a general landmark pair based on the distance information of the unfixed point and the fixed point.

Alternatively, whether a general landmark pair is formed may be further strictly judged by using the local image similarities around each of the unfixed points that are determined as forming a general landmark pair based on the distance information of the unfixed point and the fixed point.

Moreover, in the explanation according to the present embodiment, all the unfixed points that are not entered into the fixed points are deleted from the tentative landmark pair group. However, the present invention is not limited thereto. Among the unfixed points that are not entered into the fixed points, only the last unfixed point of the minimum distance sequence may be added into a tentative landmark group that is established next, without being deleted. For example, when the second and fifth unfixed points in the minimum distance sequence of Group A are not entered into the fixed points, and the first and fourth unfixed points in the minimum distance sequence of Group B are not entered into the fixed points, the fifth unfixed point in the minimum distance sequence of Group A and the fourth unfixed point in the minimum distance sequence of Group B may be added to the next tentative landmark group.

In FIG. 1, the coordinate transformation parameter calculating unit 30f calculates and determines coordinate transformation parameters that are used to perform the registration of the past three-dimensional medical image (image A) and the recent three-dimensional medical image (image B), based on the positional information of the reference landmark pairs for which associations are established by the reference landmark extracting and pairing unit 30c and the general landmark pairs for which associations are established by the landmark pair forming unit 30e. In the following description, "m pairs" of the reference landmark pairs and the general landmark pairs are formed in total. Moreover, the reference landmark pairs and the general landmark pairs may be referred to as landmark pairs.

For example, it is assumed that the coordinates of a fixed point "ri" on the past three-dimensional medical image that constitutes a "landmark pair i (where i is an integer between 1 and m)" are (ri1, ri2, ri3), and that the coordinates of a fixed point "ti" on the recent three-dimensional medical image that constitutes the "landmark pair i" are (ti1, ti2, ti3). Then, the coordinate transformation parameter calculating unit 30f establishes simultaneous equations for a X-coordinate difference "ti1−ri1" being "a1ri1+b1ri2+c1ri3+d1", a Y-coordinate difference "ti2-ri2" being "a2ri1+b2ri2+c2ri3+d2", and a Z-coordinate difference "ti3−ri3" being "a3ri1+b3ri2+c3ri3+d3", and defines twelve coordinate transformation parameters of "a1, b1, c1, a2, b2, c2, a3, b3, c3, d1, d2, and d3".

More specifically, as indicated in FIG. 6, the coordinate transformation parameter calculating unit 30f determines the coordinate transformation parameters "a1, b1, c1, a2, b2, c2, a3, b3, c3, d1, d2, and d3" that satisfy the number "m" of simultaneous equations established for the number "m" of landmark pairs (landmark pairs 1 to m) by linear optimization such as the method of least squares.

Here, the coordinate transformation equations in FIG. 6 are simultaneous linear equations, where (t11, t12, t13) to (tm1, tm2, tm3) and (r11, r12, r13) to (rm1, rm2, rm3) are known values, while twelve coordinate transformation parameters are unknown. If four landmark pairs or more are supplied, the twelve coordinate transformation parameters can be determined by linear optimization such as the least-squares method. Furthermore, even with three landmark pairs or less, the twelve coordinate transformation parameters can be obtained with a generalized inverse matrix method. In the explanation of the present embodiment, the coordinate transformation parameters are determined in accordance with simultaneous linear equations, but the present invention is not limited thereto. For example, the coordinate transformation parameters may be determined in accordance with more complex coordinate transformation equations such as simultaneous quadratic polynomial equations.

In FIG. 1, the corresponding sectional view creating unit 30g creates corresponding sectional views of the past three-dimensional medical image (image A) and the recent three-dimensional medical image (image B), in accordance with the coordinate transformation parameters that are determined by the coordinate transformation parameter calculating unit 30f. Here, the corresponding sectional view creating unit 30g is equivalent to the "corresponding image creating unit" recited in the claims.

For example, when the user designates, of the two three-dimensional medical images designated by the user by way of the input unit 30a, a specific sectional view (image A display screen) of the past three-dimensional medical image (image A) by way of the input unit 30a and makes a request for displaying it together with a corresponding sectional view (image B display screen) of the recent three-dimensional medical image (image B) on the monitor screen of the displaying unit 30b, the corresponding sectional view creating unit 30g first creates the image A display screen in accordance with the following process.

First, as indicated in FIG. 7, the corresponding sectional view creating unit 30g determines coordinates (r1, r2, r3) of the past three-dimensional medical image (image A) that corresponds to a pixel (i, j) of the image A display screen. Then, a pixel value "vr" of the coordinates (r1, r2, r3) is obtained, and a brightness value of a display pixel is determined by conducting a gray-scale transforming process on the pixel value "vr". The corresponding sectional view creating unit 30g conducts this process on all the display pixels so that the image A display screen that is to be displayed on the monitor screen of the displaying unit 30b can be created.

Thereafter, the corresponding sectional view creating unit 30g determines the brightness value of the pixel (i, j) on the image B display screen that corresponds to the brightness value of the pixel (i, j) on the image A display screen. In other words, the corresponding sectional view creating unit 30g determines coordinates (t1, t2, t3) of the recent three-dimensional medical image (image B) that corresponds to the coordinates (r1, r2, r3) of the past three-dimensional medical image (image A), as illustrated in FIG. 7, in accordance with the coordinate transformation equations using the coordinate transformation parameters determined by the coordinate transformation parameter calculating unit 30f. Then, a pixel value "vt" of the coordinates (t1, t2, t3) of the recent three-dimensional medical image (image B) is obtained, and the brightness value of the pixel (i, j) on the image B display screen is determined by gray-scale transformation. The corresponding sectional view creating unit 30g executes this process on all the display pixels to create the image B display screen that is to be displayed on the monitor screen of the displaying unit 30b.

In FIG. 1, the display controlling unit 30h performs control to display the corresponding sectional views of the past three-dimensional medical image (image A) and the recent three-dimensional medical image (image B) that are created by the corresponding sectional view creating unit 30g on the monitor screen of the displaying unit 30b. Here, the display controlling unit 30h corresponds to the "display controlling unit" recited in the claims.

Figure 8:
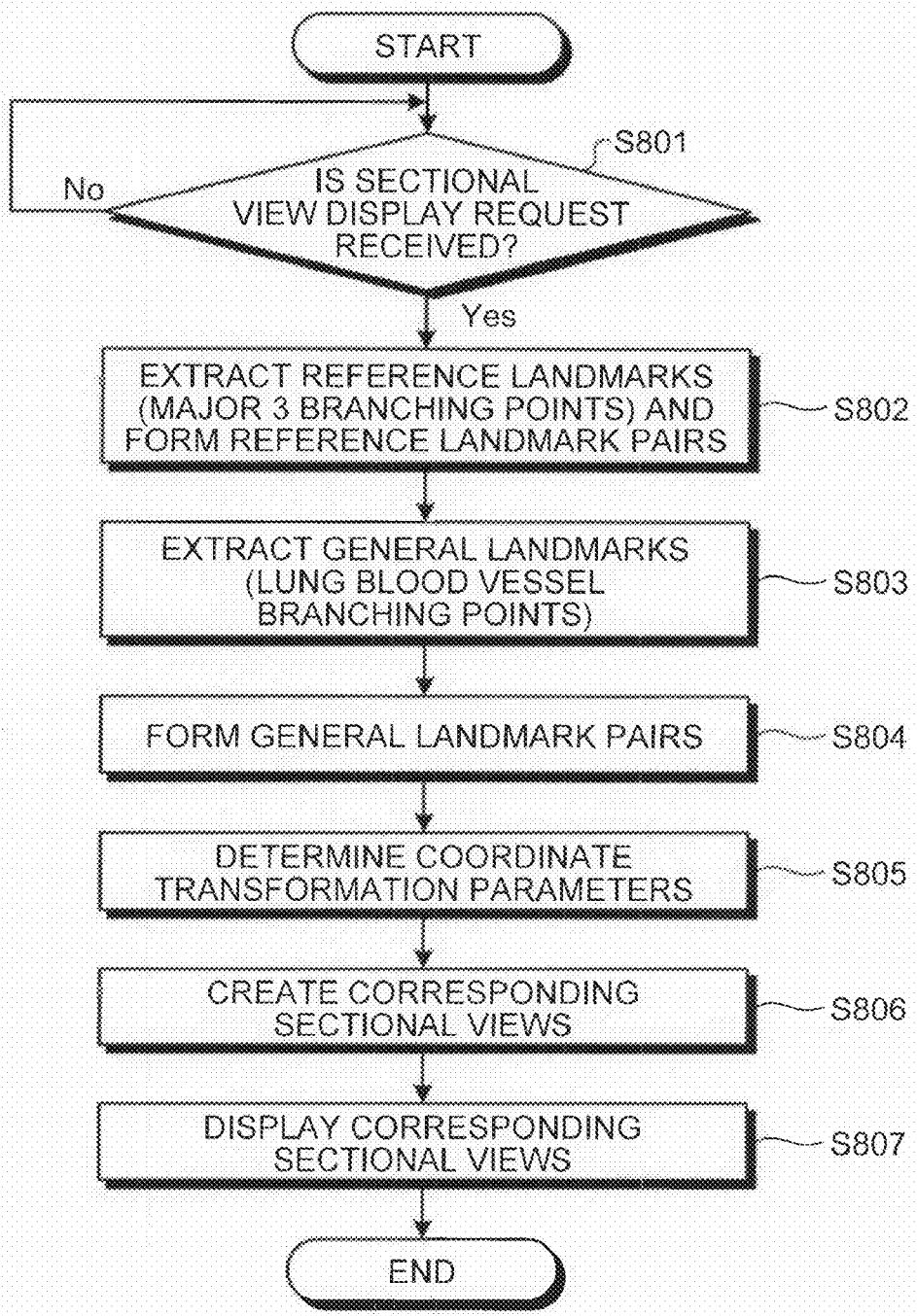
FIG. 8 is a diagram for explaining a process conducted by the medical image display device according to the first embodiment.

Next, the process performed by the medical image display device 30 according to the first embodiment is explained with reference to FIG. 8. FIG. 8 is a diagram for explaining the process performed by the medical image display device according to the first embodiment.

As indicated in FIG. 8, when the medical image display device 30 according to the first embodiment receives a sectional view display request by way of the input unit 30a from the user who performs comparison and interpretation (yes at step S801), the reference landmark extracting and pairing unit 30c extracts three reference landmarks having the "three major branching points" of the trachea and bronchi from each of the past three-dimensional medical image and the recent three-dimensional medical image, and forms reference landmark pairs from the extracted "three major branching points" of the trachea and bronchi (step S802).

Then, the general landmark extracting unit 30d extracts branching points of the lung blood vessels as general landmarks from each of the past three-dimensional medical image and the recent three-dimensional medical image (step S803).

Thereafter, the landmark pair forming unit 30e forms general landmark pairs for which associations are established between the past three-dimensional medical image and the recent three-dimensional medical image, from the group of general landmarks extracted by the general landmark extracting unit 30d (step S804, see FIG. 5).

Thereafter, the coordinate transformation parameter calculating unit 30f calculates and determines the coordinate transformation parameters to use for the registration of the past three-dimensional medical image and the recent three-dimensional medical image, based on the positional information of the reference landmark pairs for which the associations are established by the reference landmark extracting and pairing unit 30c and the general landmark pairs for which the associations are established by the landmark pair forming unit 30e (step S805).

Then, the corresponding sectional view creating unit 30g creates the corresponding sectional views of the past three-dimensional medical image and the recent three-dimensional medical image, based on the coordinate transformation parameters determined by the coordinate transformation parameter calculating unit 30f (step S806). The display controlling unit 30h performs control to display the corresponding sectional views of the past three-dimensional medical image and the recent three-dimensional medical image created by the corresponding sectional view creating unit 30g on the monitor screen of the displaying unit 30b, and thereby the two corresponding sectional views are displayed (step S807). Then, the process is terminated. Thereafter, the doctor performs comparison and interpretation by referring to the two corresponding sectional views displayed on the monitor of the displaying unit 30b.

As described above, according to the first embodiment, the reference landmark extracting and pairing unit 30c extracts the three reference landmarks having the "three major branching points" of the trachea and bronchi from each of the past three-dimensional medical image and the recent three-dimensional medical image, and forms the reference landmark pairs. The general landmark extracting unit 30d extracts the branching points of the lung blood vessels as general landmarks from each of the past three-dimensional medical image and the recent three-dimensional medical image. The landmark pair forming unit 30e forms general landmark pairs in the past three-dimensional medical image and the recent three-dimensional medical image by use of the distances of the reference landmarks and of the general landmarks, and further forms general landmark pairs from the general landmarks that are not included in the general landmarks of these general landmark pairs, by use of the distances from each of the general landmarks formed into the general landmark pairs.

Then, the coordinate transformation parameter calculating unit 30f calculates the coordinate transformation parameters, based on the positional information of the reference landmark pairs and the general landmark pairs. The corresponding sectional view creating unit 30g creates the corresponding sectional views of the past three-dimensional medical image and the recent three-dimensional medical image, based on the coordinate transformation parameters. The display controlling unit 30h performs control to display the corresponding sectional views that are created for the past three-dimensional medical image and the recent three-dimensional medical image on the monitor screen of the displaying unit 30b. As a result, even when a number of erroneous general landmarks are included, general landmark pairs can be still reliably formed, and as described above as the main characteristic feature, the registration can be accurately conducted between the three-dimensional medical images.

In other words, the "three major branching points" of the trachea and bronchi can be found in every patient, and each point can be unique determined from the anatomical aspect. For example, the first right-side branching point of the bronchi denotes a specific branching point in every patient, and understandably, the point can be uniquely determined among the radiographic data of the patient. On the other hand, the branching points of the lung blood vessels cannot be individually identified, and generally they cannot be uniquely determined. For the registration process on three-dimensional medical images of the lung area, the landmarks need to be associated with each other. However, if the landmarks cannot be uniquely identified, it is difficult to establish associations. Nevertheless, it is essential to incorporate the branching points of the lung blood vessels that range all over the lung area to improve the processing accuracy of the registration. In other words, the registration process can be executed at high speed if the uniquely identifiable landmarks only are used, but from the view point of the accuracy of the registration process, landmarks that are not uniquely identifiable but are present in a wide range should be incorporated.

Thus, according to the first embodiment, landmark pairs (reference landmark pairs) are formed by using uniquely identifiable landmarks as reference landmarks, and landmarks that are present in a wide range but cannot be uniquely identified are used as general landmarks. Then, for the general landmark pairing process, associations of the general landmarks are made by use of information of the distances (angles or degree of image similarities, alternatively) of the landmarks obtained by referring to the information of the reference landmark pairs. The associations of the general landmarks are established in this manner, with reference to the reference landmark pairs for which reliable associations can be established. Hence, the general landmarks that are not uniquely identified can be reliably brought into associations, and the registration between the three-dimensional medical images can always be conducted with high accuracy, even if the ratio of erroneously extracted general landmarks is so high that the registration would fail with the conventional technology.

According to the present embodiment, the "three major branching points" of the trachea and bronchi are used as the reference landmarks for which associations can be anatomically uniquely established, but the present invention is not limited thereto. Along with the "main trachea branching point" and the "first branching points of the bronchi", all the "second to fourth branching points of the bronchi" or part of the points may be extracted as the major branching points and used as the reference landmarks. Furthermore, in the explanation of the present embodiment, focuses the branching points of the lung blood vessels are used as the general landmarks, but the present invention is limited thereto. As general landmarks, in a similar manner to the branching points of the lung blood vessels, "bronchi branching points (such as branching points after the fifth branching point of the bronchi) " that are present in a wide range, other than the "three major branching points" of the trachea and bronchi, may be used.

[Second Embodiment]

According to the first embodiment that is described above, the branching points of the lung blood vessels are adopted for general landmarks. The second embodiment is explained with reference to FIGS. 9 and 10, where the "branching points of the bronchi" other than the "three major branching points" of the trachea and bronchi are adopted as general landmarks in addition to the branching points of the lung blood vessels. Here, FIG. 9 is a diagram for explaining the concept of the medical image display device according to the second embodiment, and FIG. 10 is a diagram for explaining a general landmark extracting unit according to the second embodiment.

The medical image display device 30 according to the second embodiment is configured to have the same structure as that of the medical image display device 30 according to the first embodiment described in FIG. 1, but the process performed by the general landmark extracting unit 30d and the landmark pair forming unit 30e differ. In the following, the difference is mainly discussed.

Figure 9:
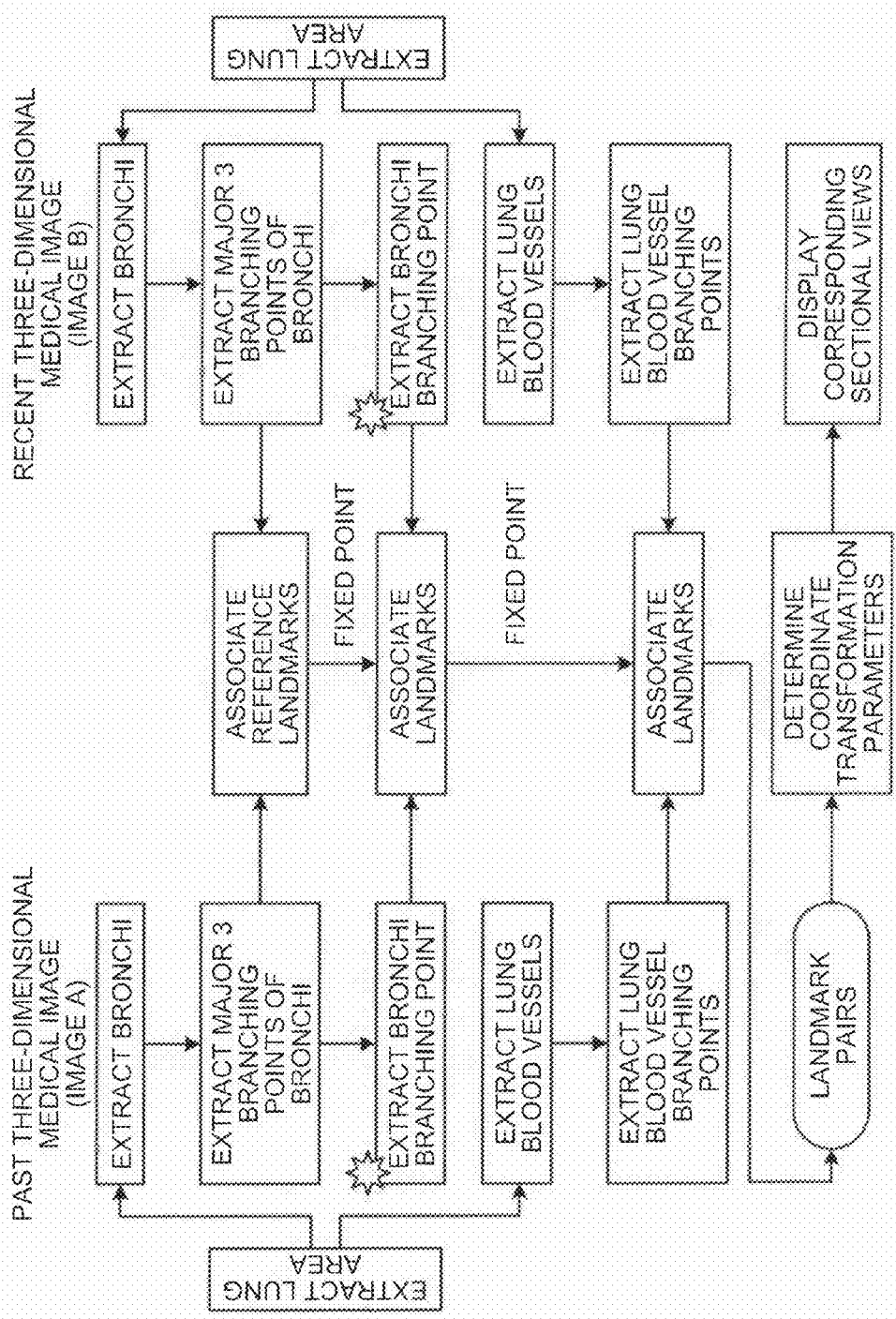
FIG. 9 is a diagram for explaining the concept of a medical image display device according to a second embodiment.
Figure 10:
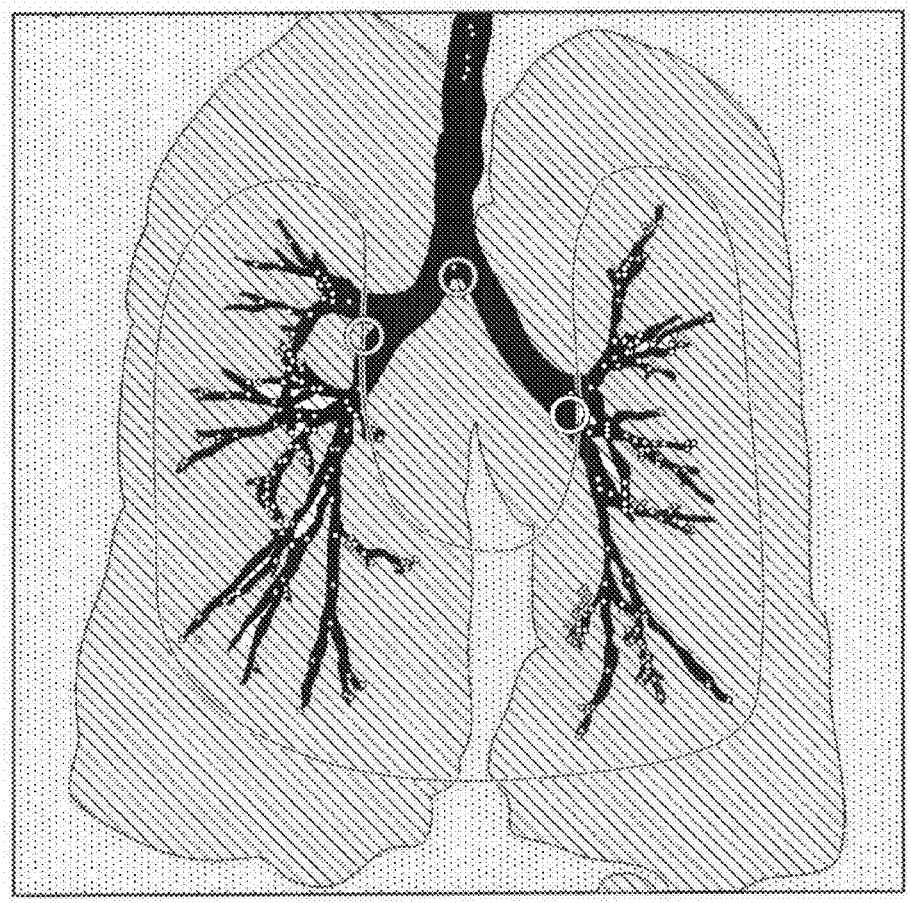
FIG. 10 is a diagram for explaining a general landmark extracting unit according to the second embodiment.

First, in the medical image display device 30 according to the second embodiment, the reference landmark extracting and pairing unit 30c extracts the lung area from each of the past three-dimensional medical image (image A) and the recent three-dimensional medical image (image B), and extracts three reference landmarks having "three major branching points", as described in FIG. 9, in the same manner as in the first embodiment. The reference landmark extracting and pairing unit 30c establishes associations among the extracted reference landmarks, and enters them into fixed points.

Here, the general landmark extracting unit 30d included in the medical image display device 30 according to the second embodiment is different from that of the first embodiment. As indicated in FIG. 9, the branching points of the bronchi other than the "three major branching points" (hereinafter, "bronchi branching points") are extracted as general landmarks. For example, as illustrated in FIG. 10, the "bronchi branching points" (see open circles) other than the "three major branching points" (see double circles) are extracted. The "bronchi branching points" correspond to the "minor branching points" recited in the claims.

Then, as indicated in FIG. 9, the landmark pair forming unit 30e included in the medical image display device 30 according to the second embodiment establishes general landmark associations of the multiple "bronchi branching points" by the same process as the one illustrated in FIG. 5, thereby extracting general landmark pairs, determining the extracted general landmark pairs as reference landmark pairs, and entering the "bronchi branching points" that form the reference landmark pairs into fixed points.

Thereafter, as indicated in FIG. 9, the general landmark extracting unit 30d included in the medical image display device 30 according to the second embodiment extracts the lung blood vessel area in the same manner as in the first embodiment, and extracts the branching points of the lung blood vessels as general landmarks.

Then, as indicated in FIG. 9, the landmark pair forming unit 30e included in the medical image display device 30 according to the second embodiment establishes general landmark associations of the multiple branching points of the lung blood vessels, extracts general landmark pairs, and enters the branching points of the lung blood vessels that form the extracted general landmark pairs as the fixed points, in a similar process to the one indicated in FIG. 5.

Then, as indicated in FIG. 9, the coordinate transformation parameter calculating unit 30f calculates and determines the coordinate transformation parameters by using the positional information of the landmark pairs including the reference landmark pairs and the general landmark pairs. The corresponding sectional view creating unit 30g creates the corresponding sectional views of the past three-dimensional medical image and the recent three-dimensional medical image, and the displaying unit 30b displays the two corresponding sectional views on its monitor screen in accordance with the control performed by the display controlling unit 30h.

Figure 11:
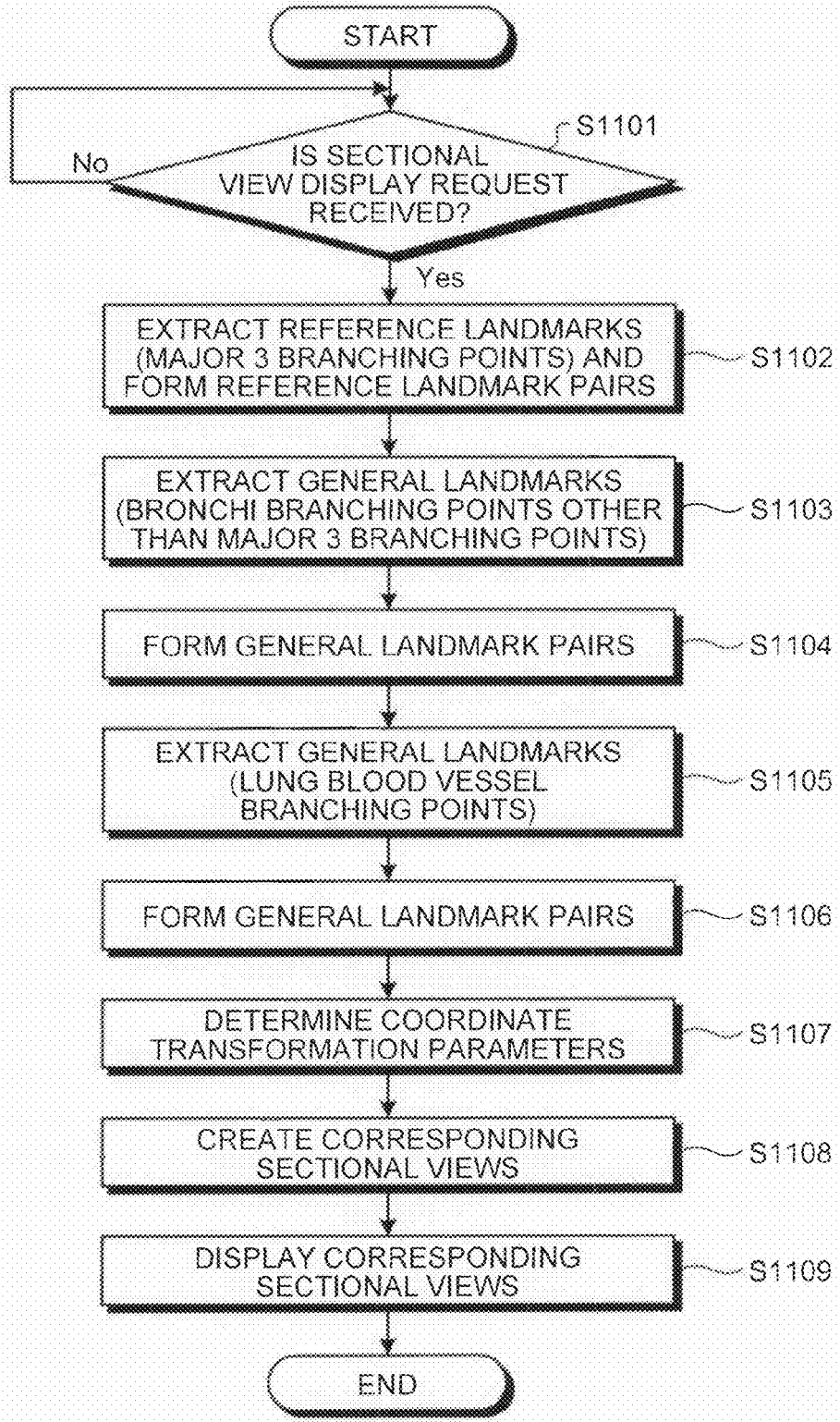
FIG. 11 is a diagram for explaining a process conducted by the medical image display device according to the second embodiment.
Figure 13:
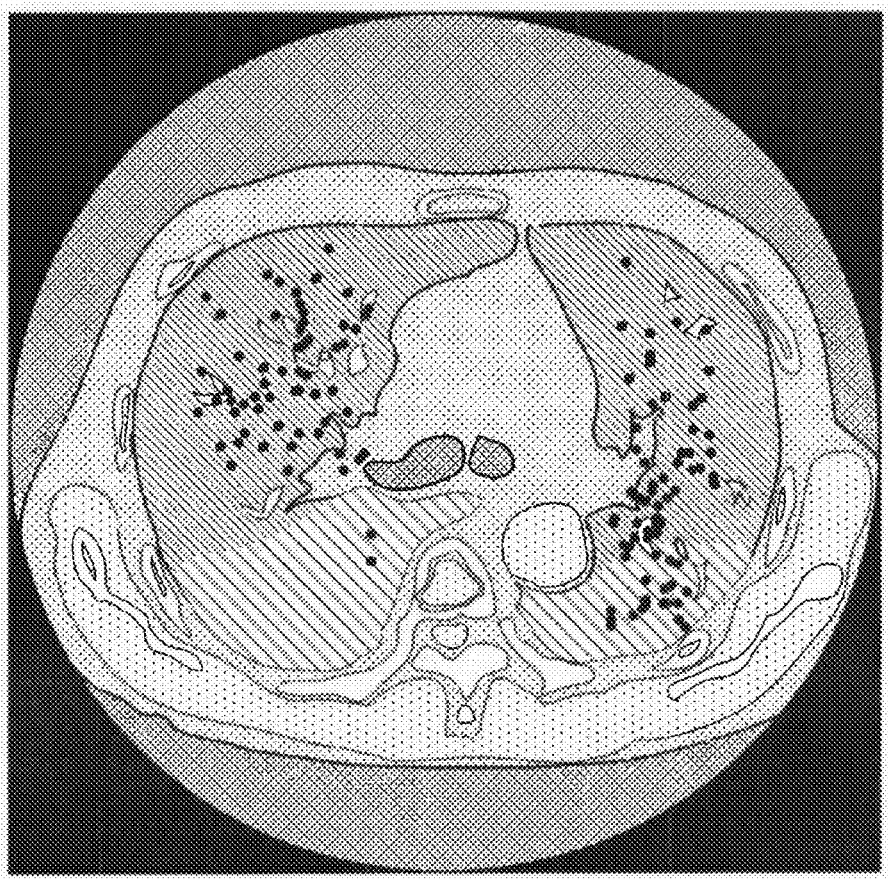
FIG. 13 is a diagram for explaining problems in the conventional technology.

Next, the process performed by the medical image display device 30 according to the second embodiment is explained with reference to FIG. 11. FIG. 11 is a diagram for explaining the process performed by the medical image display device according to the second embodiment.

As described in FIG. 11, when the medical image display device 30 according to the second embodiment receives a sectional view display request by way of the input unit 30a from the user who conducts comparison and interpretation (yes at step S1101), the reference landmark extracting and pairing unit 30c extracts the three reference landmarks having the "three major branching points" from each of the past three-dimensional medical image and the recent three-dimensional medical image, and forms the reference landmark pairs from the extracted "three major branching points" (step S1102).

Then, the general landmark extracting unit 30d extracts the "bronchi branching points" other than the "three major branching points" as general landmarks from each of the past three-dimensional medical image and the recent three-dimensional medical image (step S1103). The landmark pair forming unit 30e forms general landmark pairs for which associations are established between the past three-dimensional medical image and the recent three-dimensional medical image from the multiple "bronchi branching points" extracted by the general landmark extracting unit 30d other than the "three major branching points" (step S1104), and determines these general landmark pairs as the reference landmark pairs.

Thereafter, the general landmark extracting unit 30d extracts the branching points of the lung blood vessels as general landmarks from each of the past three-dimensional medical image and the recent three-dimensional medical image (step S1105). The landmark pair forming unit 30e forms general landmark pairs for which associations are established between the past three-dimensional medical image and the recent three-dimensional medical image, from the multiple branching points of the lung blood vessels that are extracted by the general landmark extracting unit 30d (step S1106).

Thereafter, the processes at steps S1107 to 51109 are the same as the processes at steps S805 to S807 described in FIG. 8, and thus the explanation is omitted.

As discussed above, according to the second embodiment, the "bronchi branching points" and the branching points of the lung blood vessels that are present in a wide range of the lung area are both used as general landmarks, and these general landmarks are sequentially paired on the basis of the information on the positions with respect to the reference landmarks to create the corresponding sectional views. Thus, the registration between the three-dimensional medical images can be further accurately performed.

[Third Embodiment]

According to the first embodiment that is discussed above, the reference landmark pairs and the general landmark pairs are equally evaluated when the coordinate transformation parameters are determined. The third embodiment is now explained with reference to FIG. 12, where coordinate transformation parameters are determined by giving different evaluations to the reference landmark pairs and the general landmark pairs. Here, FIG. 12 is a diagram for explaining a coordinate transformation parameter calculating unit according to the third embodiment.

The medical image display device 30 according to the third embodiment has the same structure as the medical image display device 30 according to the first embodiment illustrated in FIG. 1, but the process performed by the coordinate transformation parameter calculating unit 30f differs. The following explanation focuses on this difference.

The coordinate transformation parameter calculating unit 30f included in the medical image display device 30 according to the third embodiment assigns larger weights to the positional information of the reference landmark pairs than to the positional information of the general landmark pairs, and calculates and determines the coordinate transformation parameters.

More specifically, the coordinate transformation parameter calculating unit 30f included in the medical image display device 30 according to the third embodiment is different from that of the first embodiment in that both sides of each of the number "m" of simultaneous equations of FIG. 6 that are established on the basis of the positional information of the number "m" of landmark pairs are multiplied by weights "w1, w2, . . . , wm", as indicated in FIG. 12. Here, if all the weights "w1, w2, . . . , wm" are "1", they would be the same as in the first embodiment. However, according to the third embodiment, the weight "10" is assigned to the primary expression of each reference landmark pair, and the weight "1" is assigned to the primary expression of each general landmark pair. Then, coordinate transformation parameters "a1, b1, c1, a2, b2, c2, a3, b3, c3, d1, d2, and d3" that satisfy the number "m" of simultaneous equations are determined by linear optimization such as the least-square method.

The process procedure of the medical image display device 30 according to the third embodiment is the same as the process procedure of the medical image display device 30 according to the first embodiment, except for the above process performed by the coordinate transformation parameter calculating unit 30f at step S805 of FIG. 8. Thus, the explanation is omitted.

As discussed above, according to the third embodiment, a larger weight is assigned to the reference landmark pairs than to the general landmark pairs. For example, the weight assigned to the reference landmark pairs is determined as "10", while the weight assigned to the general landmark pairs is determined as "1". Thus, the influence of the three reference landmarks is the "square of 10" times that of each of the general landmarks of the extracted general landmark pairs. Thus, even if the branching points of the lung blood vessels extracted as the general landmark pairs are actually erroneously extracted false branching points of the lung blood vessels, their influence on the registration between the three-dimensional medical images can be reduced. In other words, according to the present embodiment, the assignment of weights can be modified in accordance with the types of landmarks, and therefore the accuracy of the registration can be still maintained even when an error occurs in the landmark detection.

In the above explanation of the first to third embodiments, the past three-dimensional medical image is defined as the "first three-dimensional medical image", and the recent three-dimensional medical image is defined as the "second three-dimensional medical image", but the present invention is not limited thereto. The recent three-dimensional medical image may be defined as the "first three-dimensional medical image", and the past three-dimensional medical image may be defined as the "second three-dimensional medical image".

In addition, in the above explanation of the first to third embodiments, when the user designates a sectional view of the past three-dimensional medical image, a display image for the past three-dimensional medical image is created, and then a display image for the recent three-dimensional medical image is created in accordance with the coordinate transformation equations incorporating the determined coordinate transformation parameters, but the present invention is not limited thereto. A display image for the recent three-dimensional medical image may be crated when the sectional view of the recent three-dimensional medical image is designated, and then a display image for the past three-dimensional medical image may be created in accordance with the coordinate transformation equations incorporating the determined coordinate transformation parameters.

Furthermore, according to the first to third embodiments, the "three major branching points" of the trachea and bronchi are adopted as reference landmarks, but the present invention is not limited thereto. For example, in a similar manner to the "three major branching points" of the trachea and bronchi, the apex of lung, which exists in every patient and is anatomically uniquely identifiable, may be adopted for the reference landmark.

Moreover, in the above explanation of the first to third embodiments, X-ray CT images are used as the three-dimensional medical images that are to be registered, but the present invention is not limited thereto. The registration may be performed on MRI images, PET images, SPECT images, ultrasonic images, and the like as the three-dimensional medical images.

Furthermore, in the above explanation of the first to third embodiments, the "three major branching points" of the trachea and bronchi are adopted as the reference landmarks to be used as references in the registration of the three-dimensional medical images including the lung area, but the present invention is not limited thereto. For example, the top end of the spinous process may be adopted as a reference landmark to be used as a reference in the registration of three-dimensional medical images including the spine. Any landmark that can be anatomically uniquely identified in tissue included in three-dimensional medical images may be selected as a reference landmark and used as a registration reference.

In addition, the structural components of the devices are conceptually and functionally illustrated, and thus may not be physically configured in the same manner as illustrated in the drawings. In other words, concrete forms of separation and integration of the devices are not limited to the illustrated ones, and all or part of them may be functionally or physically separated or integrated in any arbitrary units in accordance with various loads and usage conditions. Furthermore, all or any part of the processing functions performed by the devices may be realized by the CPU and programs analyzed and implemented by the CPU, or may be realized as hardware by a wired logic circuit.

The image displaying method explained in the present embodiments can be realized by implementing a prepared program on a computer such as a personal computer and a workstation. Such a program may be distributed by way of a network such as the Internet. In addition, the program may be stored in a computer readable recording medium such as a hard disk, a flexible disk (FD), a CD-ROM, a MO, and a DVD, and read from the recording medium by a computer to be implemented.

Industrial Applicability

As discussed above, the medical image display device and the image displaying method according to the present invention are useful when registering two three-dimensional medical images and displaying corresponding images of the two three-dimensional medical images, and it is suitable especially for always performing registration between the three-dimensional medical images with high accuracy.

The invention claimed is:

1. A medical image display device, comprising:
a reference feature point extracting and pairing unit implemented by the medical image display device configured to extract reference feature points that are feature points identifying association between a first and a second three-dimensional medical images of a same subject and serving as references in registration individually from the first and the second three-dimensional medical images, and form a reference feature point pair in which extracted reference feature points are associated with each other, the reference feature points are major branching points of a trachea and bronchi and are fixed points for use in the registration;
general feature point extracting unit implemented by the medical image display device configured to extract general feature points that are feature points possible to use in the registration individually from the first and the second three-dimensional medical images, the general feature points are branching points other than the major branching points and have a possibility to enter as the fixed points;
a general feature point pairing unit implemented by the medical image display device configured to form a general feature point pair in which association is established between the first and the second three-dimensional medical images, from the general feature points extracted by the general feature point extracting unit, based on positional relationship with respect to the reference feature points extracted by the reference feature point extracting and pairing unit individually from the first and the second three-dimensional medical images;
a coordinate transformation parameter determining unit implemented by the medical image display device configured to determine a coordinate transformation parameter that is to be used to perform the registration between the first and the second three-dimensional medical images, based on positional information of the reference feature point pair for which the association is established by the reference feature point extracting and pairing unit and the general feature point pair for which the association is established by the general feature point pairing unit, the coordinate transformation parameter is a parameter determined by using the reference feature points as fixed points and general feature points entered as the fixed points;
a corresponding image creating unit implemented by the medical image display device configured to create corresponding images for the first and the second three-dimensional medical images, based on the coordinate transformation parameter determined by the coordinate transformation parameter determining unit; and
a display controlling unit implemented by the medical image display device configured to perform control so that the corresponding images of the first and the second three-dimensional medical images created by the corresponding image creating unit are displayed on a predetermined displaying unit that displays images.

2. The medical image display device according to claim 1, wherein the general feature point pairing unit is configured to form the general feature point pair by using a distance between each of the reference feature points extracted by the reference feature point extracting and pairing unit and each of the general feature points extracted by the general feature point extracting unit in the first and the second three-dimensional medical images, and further forms an additional general feature point pair from unfixed points of the general feature points which are not included in the general feature point pair by further using a distance between each of the unfixed points and each of the fixed points which are the reference points and the general feature points included in the general feature point pair.

3. The medical image display device according to claim 1, wherein:
the general feature point extracting unit is configured to extract branching points of the trachea and bronchi other than the major branching points or branching points of lung blood vessels, as the general feature points.

4. The medical image display device according to claim 1, wherein:
the general feature point extracting unit is configured to extract minor branching points that are branching points of the trachea and bronchi other than the major branching points and branching points of lung blood vessels, as the general feature points; and
the general feature point pairing unit is configured to form the general feature point pair from the minor branching points that serve as the general feature points by using a distance between each of the reference feature points which are the fixed points and each of the minor branching points, enter the minor branching points that form the general feature point pair as the fixed point, and form the general feature point pair from the branching points of the lung blood vessels that serve as the general feature points by using a distance between each of the fixed points and each of the branching points of the lung blood vessels.

5. The medical image display device according to claim 1, wherein the coordinate transformation parameter determining unit is configured to assign a larger weight to positional information of the reference feature point pair than positional information of the general feature point pair, and determines the coordinate transformation parameter.

6. An image displaying method implemented by a computer processing device, comprising:
by a reference feature point extracting and pairing unit implemented by the processing device, extracting reference feature points that are feature points identifying association between a first and a second three-dimensional medical images of a same subject and serving as references in registration individually from the first and the second three-dimensional medical images, and forming a reference feature point pair in which extracted reference feature points are associated with each other, the reference feature points are major branching points of a trachea and bronchi and are fixed points for use in the registration;

by a general feature point extracting unit implemented by the processing device, extracting general feature points that are feature points possible to use in the registration individually from the first and the second three-dimensional medical images, the general feature points are branching points other than the major branching points and have a possibility to enter as the fixed points;

by a general feature point pairing unit implemented by the processing device, forming a general feature point pair in which association is established between the first and the second three-dimensional medical images from the general feature points extracted at the general feature point extracting step, based on positional relationship with respect to the reference feature points extracted from each of the first and the second three-dimensional medical images at the reference feature point extracting and pairing step;

by a coordinate transformation parameter determining unit implemented by the processing device, determining a coordinate transformation parameter that is to be used to perform the registration between the first and the second three-dimensional medical images, based on positional information of the reference feature point pair for which the association is established at the reference feature point extracting and pairing step and the general feature point pair for which the association is established at the general feature point pairing step, the coordinate transformation parameter is a parameter determined by using the reference feature points as fixed points and general feature points entered as the fixed points;

by a corresponding image creating unit implemented by the processing device, creating corresponding images for the first and the second three-dimensional medical images, based on the coordinate transformation parameter determined at the coordinate transformation parameter determining step; and by a display controlling unit implemented by the processing device, performing control so that the corresponding images of the first and the second three-dimensional medical images created at the corresponding image creating step are displayed on a predetermined displaying unit.

7. The image displaying method according to claim 6, wherein the method further comprises forming, using the general feature point pairing unit, the general feature point pair by using a distance between each of the reference feature points extracted by the reference feature point extracting and pairing unit and each of the general feature points extracted by the general feature point extracting unit in the first and the second three-dimensional medical images, and further forming an additional general feature point pair from unfixed points of the general feature points which are not included in the general feature point pair by further using a distance between each of the unfixed points and each of the fixed points which are the reference points and the general feature points included in the general feature point pair.

8. The image displaying method according to claim 6, wherein the method further comprises:

extracting, using the general feature point extracting unit, branching points of the trachea and bronchi other than the major branching points or branching points of lung blood vessels, as the general feature points.

9. The image displaying method according to claim 6, wherein:

extracting, using the general feature point extracting unit, minor branching points that are branching points of the trachea and bronchi other than the major branching points and branching points of lung blood vessels, as the general feature points; and forming, using the general feature point pairing unit, the general feature point pair from the minor branching points that serve as the general feature points by using a distance between each of the reference feature points which are the fixed points and each of the minor branching points, enter the minor branching points that form the general feature point pair as the fixed point, and forming the general feature point pair from the branching points of the lung blood vessels that serve as the general feature points by using a distance between each of the fixed points and each of the branching points of the lung blood vessels.

10. The image displaying method according to claim 6, wherein the method further comprises assigning, using the coordinate transformation parameter determining unit, a larger weight to positional information of the reference feature point pair than positional information of the general feature point pair, and determining the coordinate transformation parameter.

11. A medical image display device, comprising:

a reference feature point extracting unit implemented by the medical image display device configured to respectively extract reference points from first and second three-dimensional medical images of a same subject, the reference points representing major branching points of a trachea and bronchi and providing references in registration of the first and second three-dimensional medical images;

a reference feature point pairing unit implemented by the medical image display device configured to form a first point pair by associating a first reference point extracted from the first three-dimensional medical image and a second reference point extracted from the second three-dimensional medical image;

a general feature point extracting unit implemented by the medical image display device. configured to extract general feature points, that are distinct from the reference points, from the first and second three-dimensional medical images of the same subject, the general feature points providing references in registration of the first and second three-dimensional medical images;

a general feature point pairing unit implemented by the medical image display device configured to form a second point pair by associating a first general feature point extracted from the first three-dimensional medical image and a second general feature point extracted from the second three-dimensional medical image, the associating verifying a correlation based on a positional relationship between the first general feature point and a respective reference point in the first three-dimensional medical image, and a positional relationship between the second general feature point and a respective reference point in the second three-dimensional medical image;

a coordinate transformation parameter determining unit implemented by the medical image display device configured to determine a coordinate transformation parameter, for registration between the first and second three-dimensional medical images, based on positional information of the first point pair and of the second point pair;

a corresponding image creating unit implemented by the medical image display device configured to create corresponding images for the first and second three-dimensional medical images, based on the coordinate transformation parameter; and a display controlling unit implemented by the medical image display device configured to display the corresponding images of the first and second three-dimensional medical images on a predetermined displaying unit that displays images.

* * * * *